(12) United States Patent
Buncke (10) Patent No.: US 7,264,625 B1
(45) Date of Patent: Sep. 4, 2007

(54) SURGICAL CLIP APPLIER WITH REMOTE OPERATION

(76) Inventor: Harry J. Buncke, 1565 Kingswood Dr., Hillsborough, CA (US) 94010

( * ) Notice: Subject to any disclaimer, the term of this patent is extended or adjusted under 35 U.S.C. 154(b) by 1475 days.

(21) Appl. No.: 09/596,806

(22) Filed: Jun. 19, 2000

(51) Int. Cl.
*A61B 17/08* (2006.01)
(52) U.S. Cl. .................. 606/157; 606/158; 606/143
(58) Field of Classification Search ............. 606/139, 606/142, 219, 205, 143, 151, 157, 158, 153; 227/901, 902, 175.1, 602
See application file for complete search history.

(56) References Cited

U.S. PATENT DOCUMENTS

| | | | | |
|---|---|---|---|---|
| 4,485,817 A | * | 12/1984 | Swiggett | 227/179.1 |
| 4,488,523 A | * | 12/1984 | Shichman | 227/179.1 |
| 4,586,503 A | | 5/1986 | Kirsch et al. | |
| 4,610,383 A | * | 9/1986 | Rothfuss et al. | 227/19 |
| 4,646,745 A | * | 3/1987 | Noiles | 227/178.1 |
| 4,733,664 A | | 3/1988 | Kirsch et al. | |
| 4,754,909 A | * | 7/1988 | Barker et al. | 227/19 |
| 4,929,240 A | | 5/1990 | Kirsch et al. | |
| 5,174,276 A | * | 12/1992 | Crockard | 600/104 |
| 5,258,007 A | * | 11/1993 | Spetzler et al. | 606/208 |
| 5,702,048 A | * | 12/1997 | Eberlin | 227/177.1 |
| 5,720,756 A | * | 2/1998 | Green et al. | 606/143 |
| 5,779,130 A | * | 7/1998 | Alesi et al. | 227/176.1 |
| 5,868,761 A | * | 2/1999 | Nicholas et al. | 606/143 |
| 5,951,574 A | * | 9/1999 | Stefanchik et al. | 606/143 |
| 6,221,083 B1 | * | 4/2001 | Mayer | 606/139 |
| 6,443,973 B1 | * | 9/2002 | Whitman | 606/219 |
| 6,533,157 B1 | * | 3/2003 | Whitman | 227/175.1 |
| 6,599,298 B1 | * | 7/2003 | Forster et al. | 606/139 |
| 2002/0165444 A1 | * | 11/2002 | Whitman | 600/407 |
| 2002/0198541 A1 | * | 12/2002 | Smith et al. | 606/142 |

OTHER PUBLICATIONS

"Nonpenetrating Clips for Coronary Anastomosis", Patrick Nataf, M.D., et al., 1997.
"VCS Clip Application", Auto Suture Company flyer, 1995.

* cited by examiner

*Primary Examiner*—Justine R. Yu
*Assistant Examiner*—Shumaya Ali
(74) *Attorney, Agent, or Firm*—Thomas M. Freiburger (57) ABSTRACT

A surgical clip applier for use in closing wounds under the microscope in small blood vessels modifies a well-known clip applier system to make more steady and reliable the application of very small clips during surgery on a scale of vessel size of 2 mm in external diameter and smaller. The known device is modified internally so as to be capable of receiving a flexible remote actuation device which can be a cable release such as used for a camera shutter, or which can be a flexible hydraulic or pneumatic line as a force-transmitting device. Thus, the surgeon can hold the clip applier very steadily at the site desired without contracting any intrinsic muscles while the cable release is depressed by another person, or with the surgeon's other hand, or with a foot pedal.

11 Claims, 7 Drawing Sheets

SURGICAL CLIP APPLIER WITH REMOTE OPERATION

BACKGROUND OF THE INVENTION

The invention concerns surgical apparatus and techniques, and particularly relates to microsurgery, for example involving closure of blood vessels of about very small size, usually done under a microscope, or endoscopic repairs, or repairing vessels difficult to access, for example in a deep recess or hole permitting only a narrow tunnel of access.

Microsurgery, such as in plastic and reconstructive surgery, neurosurgery, replantation of limbs and appendages, hand surgery, endoscopic and arthroscopic procedures, often involves the need to suture or otherwise close wounds on extremely small tissues, including blood vessels of 2 mm external diameter and smaller. The very small vessels often need to be united or reunited together, in a procedure known as vascular anastomosis. Sometimes a large number of these anastomoses are required.

In small vessels it is usually undesirable to employ suturing, because suturing invades the interior lumen of the vessel and can cause problems of restricting blood flow and promoting clotting in the lumen.

For these reasons implements have been developed for applying very small non-penetrating clips to the walls of blood vessels. Some of these clips and application procedures are shown in Kirsch U.S. Pat. Nos. 4,586,503, 4,733,664 and 4,929,240, and these patents are incorporated herein by reference. In addition, an implement called VCS Clip Applier System is marketed by Auto Suture Company, a division of United States Surgical Corporation of Norwalk, Conn. The VCS Clip Applier has three different sizes of stems, and of clips dispensed and secured by the tips of those stems, including a small size for microsurgery applications on vessels of 2 mm external diameter and under. The VCS Clip Applier is manual and one-handed in operation. The surgeon carefully places the tip of the stem, which is forked and fed by a magazine of clips, at a position where the C-shaped clip, when applied, will engage in non-penetrating relationship against two everted layers of tissue. When the clip is dispensed it is squeezed inwardly, deforming the clip to a smaller size. To do this the surgeon squeezes together two thumb/finger wings extending out from opposite sides of the tool's handle near the tip end of the handle; this squeezing motion is effective to slide a linkage piece in the stem, causing, at the tip of the stem, inward clamping and dispensing of the clip. In a longitudinal split or line of juncture on a blood vessel or between blood vessels to be joined, the VCS Clip Applier is used to apply the clips closely and accurately together for hemostasis. The clips are left in place and need not be removed.

Particularly in the smallest version of the VCS Clip Applier, useful on blood vessels of 2 mm in external diameter and smaller, there is a problem in maintaining the stem tip steadily in position while squeezing the wings of the handle to install a clip. This is done under the microscope, and often it is difficult to apply a clip accurately. Even if the surgeon has a very steady hand, the requirement of muscle contraction to squeeze inwardly on these handle wings almost inevitably causes some small movement at the tip of the clip applier stem, at the very instant of clip application. The result is an inaccurate application of clips.

Another problem arises in use of the VCS Clip Applier, even the medium or large versions, in an awkward location such as a deep recess forming a very narrow access hole where stitches could not be made and the elongated clip applier is needed. Sometimes the narrow access does not allow the required squeezing of the thumb/finger wings, because of the excessive forward location of those wings.

A solution to these difficulties is provided by the invention described below.

SUMMARY OF THE INVENTION

In the invention described, the difficulty of holding the clip applier perfectly steadily under the microscope while applying a clip is overcome by use of a flexible cable or hydraulically tubing attached to the handle, enabling the requisite force to be applied remotely and indirectly. The invention applies to any surgical clip device in which clips are applied from the end of a stem by movement of an internal member within the handle, so as to cause movement of a clip applying component in the stem of the device, which deploys, crimps and applies a clip. In the case of the VCS clip applier described, this movement of the internal movable member is caused by squeezing the wings of the handle inwardly, but other motions could be involved.

The remote actuation provided by the invention also solves the problem of narrow access which would restrict deployment of the VCS instrument.

Thus, in a preferred embodiment of the invention a device for applying non-penetrating clips to very small blood vessels or other small tissue separation sites includes a hand-held clip applier and a flexible cable release or hydraulic actuator or other flexible remotely-actuated device for delivering a compressive pushing force to the internal movable member of the clip applier without applying force directly to the hand-held clip applier, thus isolating any vibration or unsteady movement from the clip applier tip. The clip applier in a preferred embodiment is capable of applying and securing clips to blood vessels 2 mm and under, and this clip applier may be of well-known construction such as the product Auto Suture VCS, with an important modification. The tool has a handle suitable for gripping in the hand, a clip storing and dispensing stem extending from the front end of the handle, and a tip at the end of the stem including means for dispensing and serially applying metal clips in non-penetrating engaging configuration against sections of tissue on either side of a wound or separation, to clamp the two sections together for hemostasis and regrowth. The dispensing means is activated on the receipt of an axial force to a clip-applying component of the stem.

Within the handle is a movable member which, when caused to move by a force applied from outside the handle, is effective to cause movement of the clip-applying component in the stem such as to cause dispensing and application of a clip. Further, there is a linkage of appropriate form within the handle, engaged with the movable member in the handle and extending to a position so as to be capable of receiving a pushing force from the exterior of the handle. The movable member and the linkage means can be one piece if desired. The flexible actuator, if in the form of a flexible cable release device has, a cable sheath and an internal cable capable of delivering a pushing force through the sheath, typical of a flexible cable release for a camera. A thumb button at a remote hand-grippable end of the cable release applies a pushing force to slide the cable through the sheath in order to cause extension of a pusher tail piece at a proximal end of the cable sheath when the thumb button is pushed. The proximal end of the cable sheath is secured to the clip applier tool's handle such that the pusher tail piece will apply force to the linkage means in the handle upon application of thumb pressure, thus advancing the linkage means and the movable member in the handle, and thus advancing the clip-applying component to dispense and apply a clip. This pushing force could also be supplied by a flexible hydraulic actuator, such as a syringe and tubing and sterile fluid, all standard equipment in operating rooms.

It is thus among the objects of the invention to make far more effective and reliable the use of a surgical clip applier for closing tissue separation sites, by modifying the clip applier to receive its actuating force through a flexible, remotely operated device, supplied by an assistant or via a foot-pedal, thus isolating the instrument from hand movement and allowing for use in narrow, difficult positions. Replacing the squeeze wings at the tip end of the tool handle with a remote release permits the tool to be used endoscopically or in deep inaccessible areas, by holding the tool near the base end rather than the tip of the handle, as one might handle a small paint brush or a long screwdriver. These and other objects, advantages and features of the invention will be apparent from the following description of a preferred embodiment, considered along with the accompanying drawings.

DESCRIPTION OF PREFERRED EMBODIMENTS

Figures 1, 2:
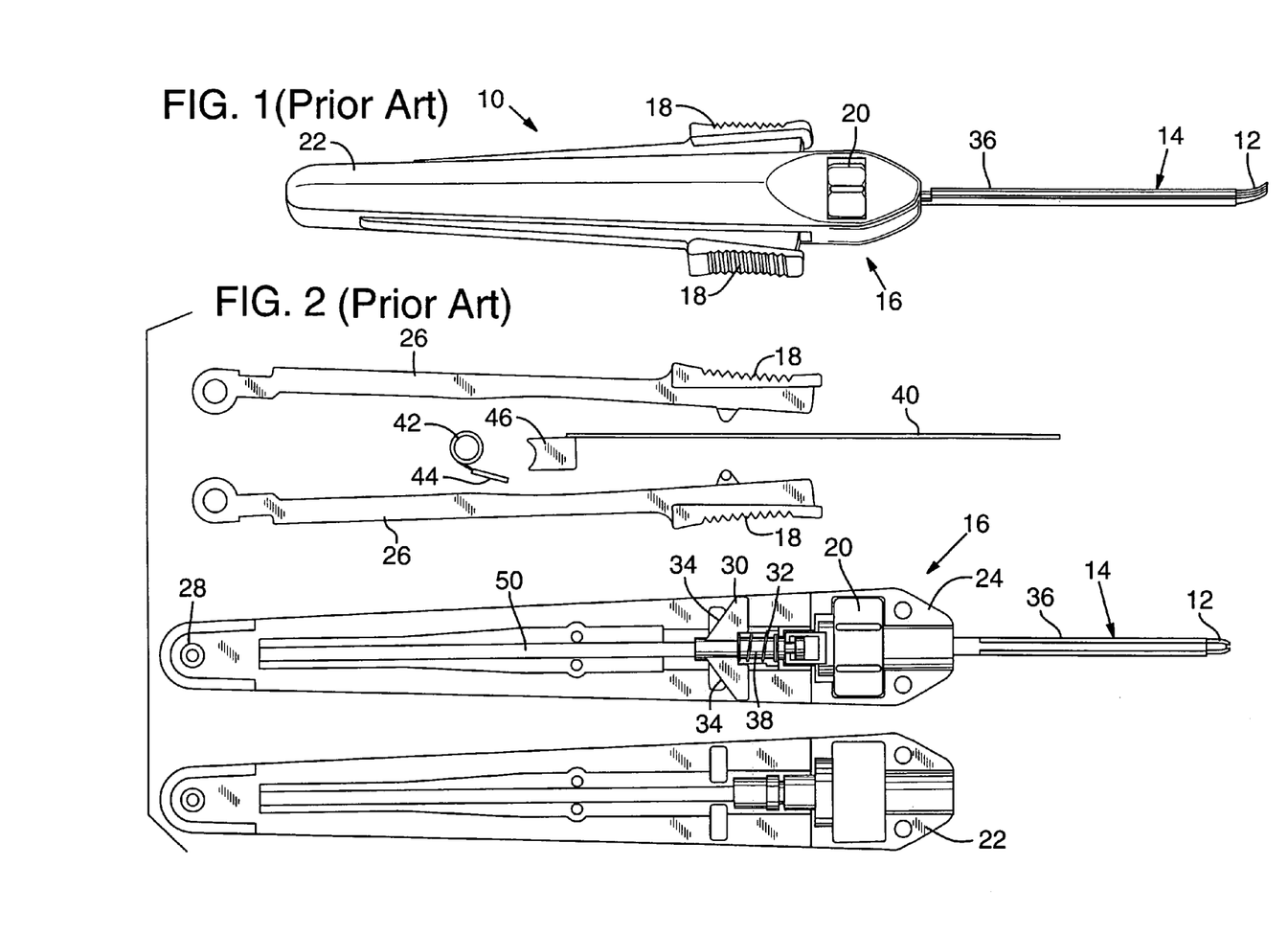
FIG. 1 is a perspective view showing a prior art clip applier with which the invention is concerned.
FIG. 2 is an exploded view showing components of the prior art clip applier.

In the drawings, FIG. 1 shows a prior art clip applier 10 of the type marketed as VCS Clip Applier by Auto Suture Company, Division of U.S. Surgical Corporation of Norwalk, Conn. This clip applier is described above and is effective to dispense and apply a small clip (clips not shown) for closure of tissues in microsurgery, from a tip 12 of a stem 14, extending from a handle 16 that the surgeon holds in the hand. As illustrated, the elongated stem 14 is much narrower than the elongated gripping handle 16 and rigidly projects forward from a forward end of the handle 16. A pair of thumb/finger wings 18 are squeezed together by the surgeon when the tip has been correctly placed and a clip is to be applied. Shortcomings of this device are described above, particularly for microsurgery on blood vessels under 2 mm or other very small surgical sites, the clip placement being performed under the microscope; and for endoscopic surgery or other use in narrow, difficult areas.

The clip applier 10 has a rotation wheel 20 to enable the surgeon to adjust the rotational orientation of the stem 14 to any desired direction. This wheel is not needed in a revised round handle described below.

FIG. 2, again showing the prior art clip applier 10, reveals the important internal components which effect clip dispensing and with which the invention is concerned. The handle 16 includes two shells or halves 22 and 24, shown disassembled in FIG. 2. The thumb/finger wings 18 are shown removed from the shells and indicating that these components have long legs 26 which pivot in the bottom end of the handle, on a pivot pin 28. When squeezed toward one another in the assembled tool, these wings 18 are effective to push outwardly by camming action a triangular-shaped hollow movable member 30 which is biased downwardly in the handle by a compression coil spring 32, toward the normal resting position shown in FIG. 2. The wings 18 when squeezed inwardly engage sloped surfaces 34 on the triangular movable member 30 to force that member upwardly, and this in turn forces upwardly (outwardly) a clip-applying component 36 which is generally C-shaped in cross section and which rides along the stem 14. When the clip-applying component slides upwardly, it causes a clip to be crimped and dispensed from the tip 12 onto the tissue to be closed or joined. The movable member 30 has a tubular stem 38 that is connected to the clip-applying component 36, so that sliding motion of the movable member 30 causes the same motion of the clip-applying component.

Figure 3:
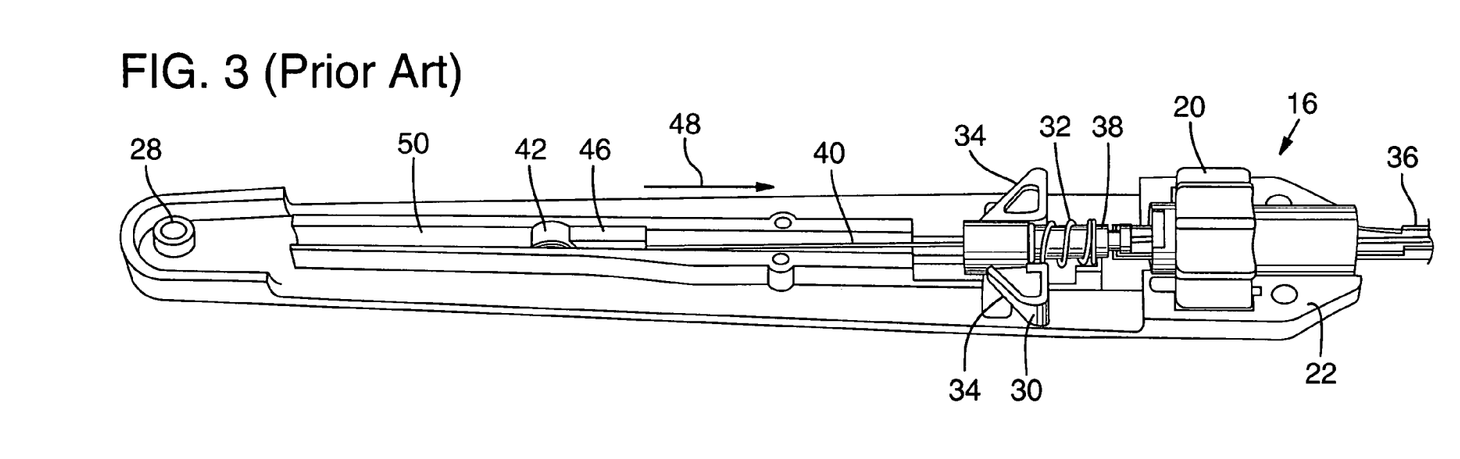
FIG. 3 is an enlarged partial view showing important internal components of the prior art clip applier, to which the invention is applicable.
Figure 4:
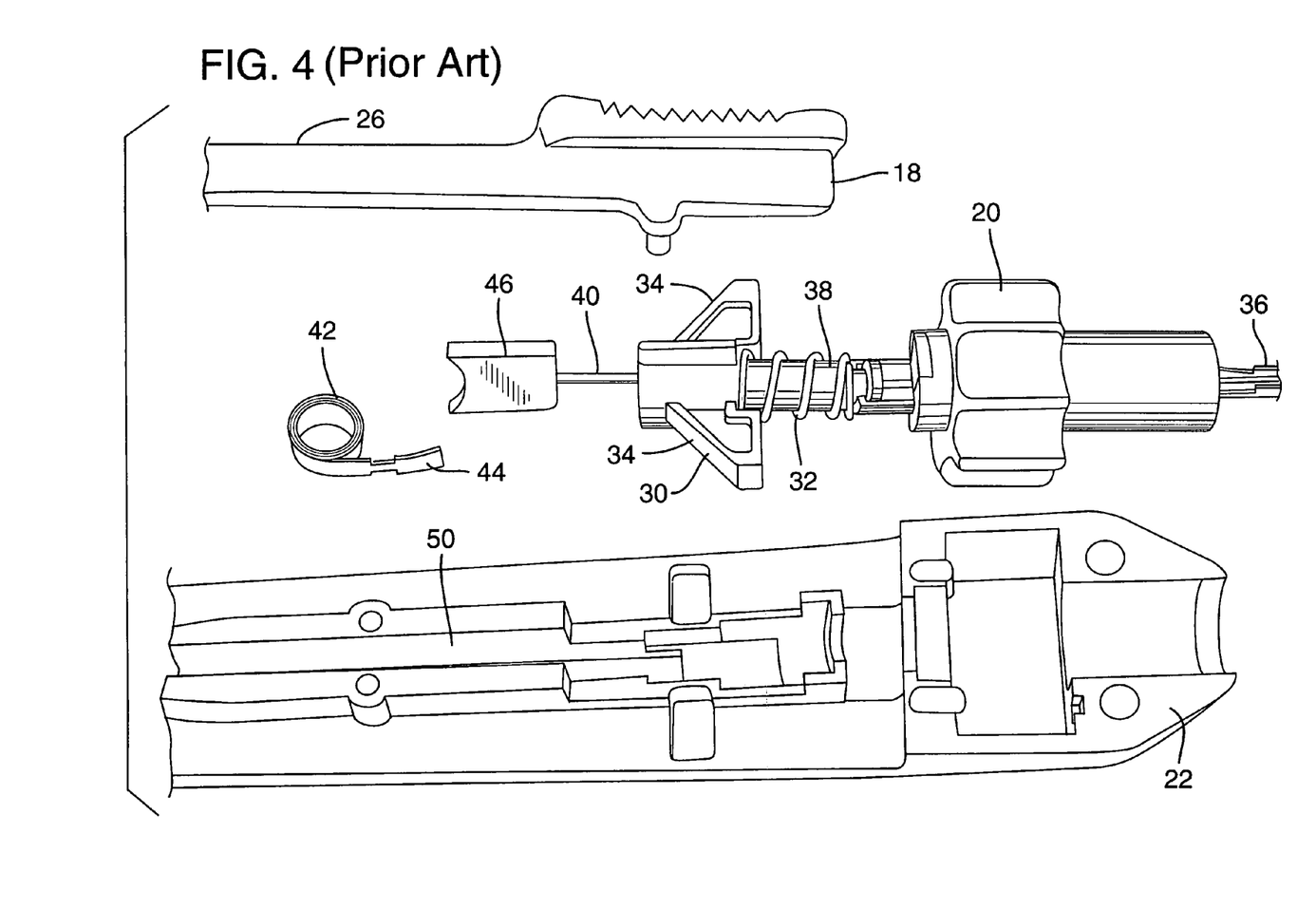
FIG. 4 is a further enlarged, exploded view showing key components of the FIG. 1 device.

As seen in FIGS. 2 and 3, the reason for the hollow movable member 30, which has a bore throughout its length, is to allow a rod 40 to pass through the member, up to near the tip of the clip applier, where it advances stored clips in a magazine in the stem, each time a clip is dispensed. The rod 40 is biased toward the advancing direction by a roll-up metal spring 42, which has a tail 44 secured in the handle and which engages against a contoured tail part 46 on the rod. FIG. 3 shows the spring 42 engaged against the contoured tail part 46, urging the rod 40 in the advancing, forward or upward direction shown by the arrow 48. The tail part 46 rides in a channel 50 formed in the handle, preferably formed in part by each of the halves. As can be seen from FIGS. 2, 3 and 4, the roll-up coil spring 42 nests against the tail part 46 on the rod and advances in the rolling-up direction to push the rod and clips forward (upward) with a relatively light pressure, until all of the clips have been dispensed.

All of the above describes the prior art VCS Clip Applier, and further details regarding the clip magazine and the manner of dispensing are not important to the understanding of the invention.

Figure 5:
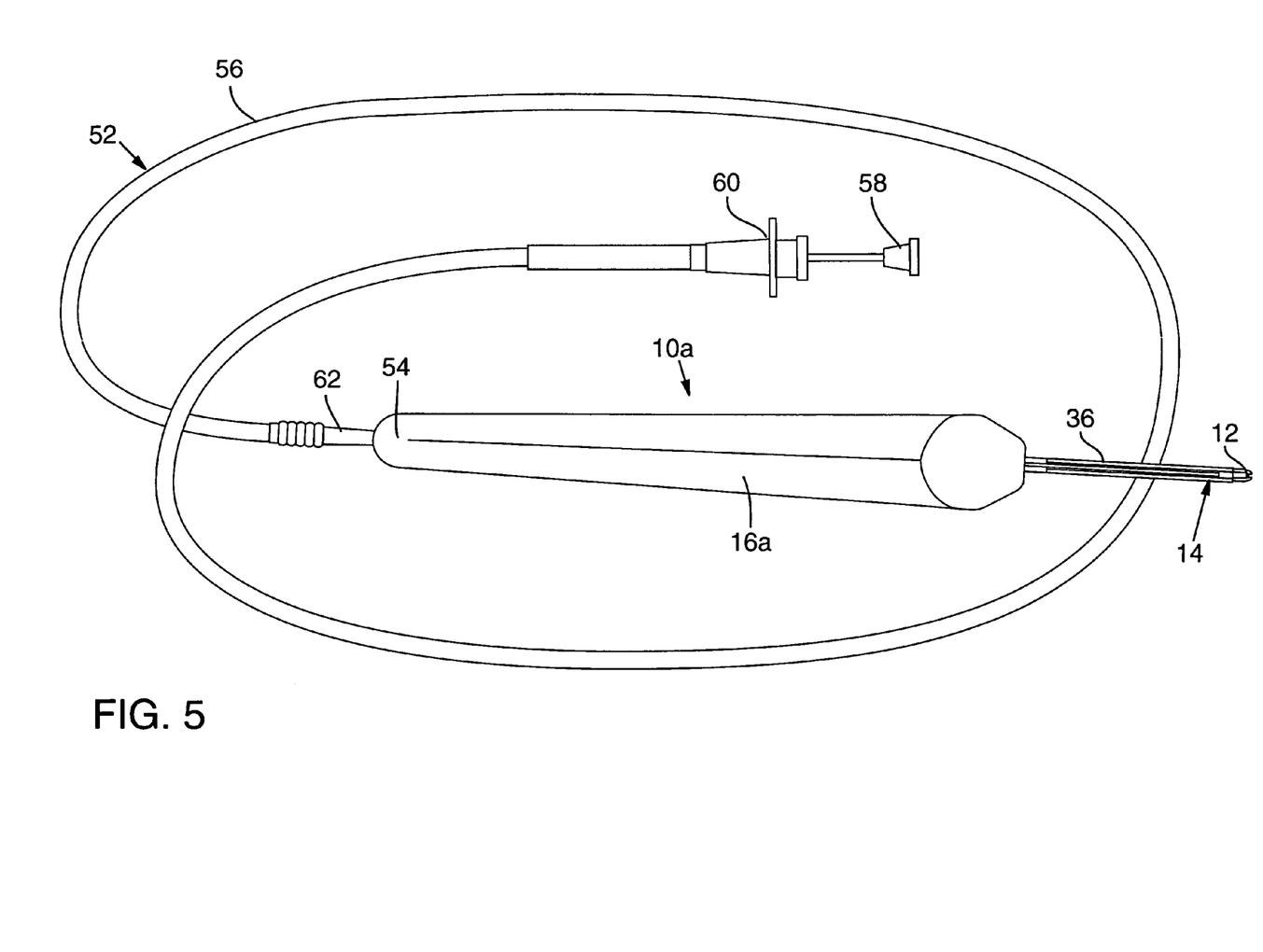
FIG. 5 is a view showing a device according to the invention, incorporating much of the prior art clip applier.

FIG. 5 shows the invention. A flexible, remote force-applying device 52, mechanical or hydraulic, is attached to a modified form of the clip applier 10a, at a tail end 54 of the tool's handle, and the thumb/finger wings 18 are eliminated. FIGS. 5-8 show the modified instrument, which preferably is cylindrical. A cylindrical handle 16a allows elimination of the swivel wheel 20, not needed when the handle is round.

As shown in FIG. 5, the remote device 52 may comprise a simple cable release useful with a camera. Such a cable release has a flexible cable sheath 56 and an internal flexible cable capable of delivering a compressive pushing force through the sheath. A thumb button 58 at a remote end of the device serves to receive thumb force, while a hand grip 60 permits comfortable gripping. Thus, the grip area 60 is held between the fingers while the thumb is used to push in on the thumb button or plunger 58, and this causes a tail piece 61

(see FIG. 6, not shown in FIG. 5) to extend out of a tail end 62, or proximal end relative to the device 10a. The tail piece as it extends from the proximal end 62 of the cable release device engages and slides forward a component in the clip applier so as to cause the clip-applying component 36 to slide forward and dispense a clip, without movement at the place of contact.

Figure 6:
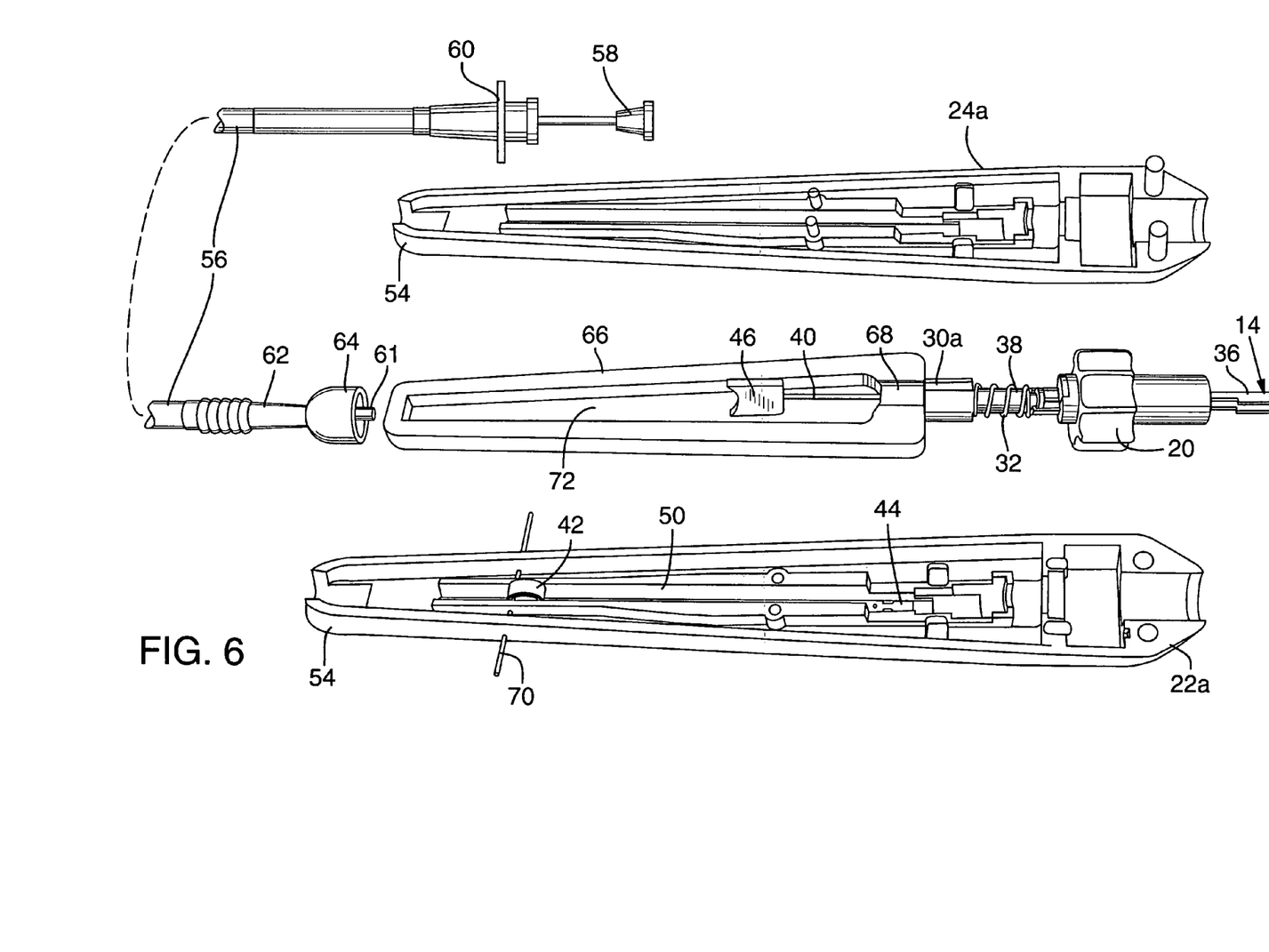
FIG. 6 is another partial exploded view of the clip applier's key components, with improvements pursuant to the invention.
Figure 7:
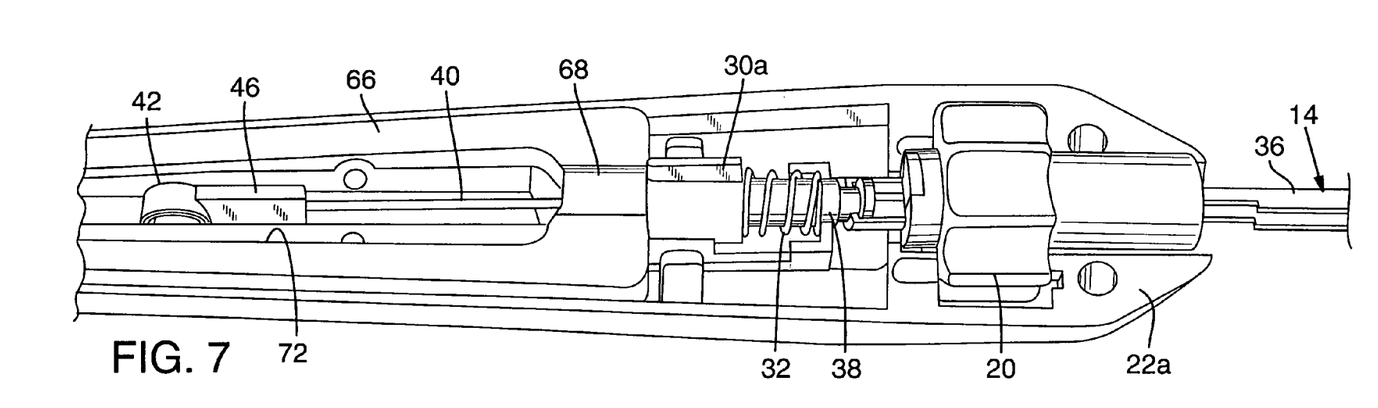
FIG. 7 is another partial view showing components of the modified clip applier.
Figure 8:
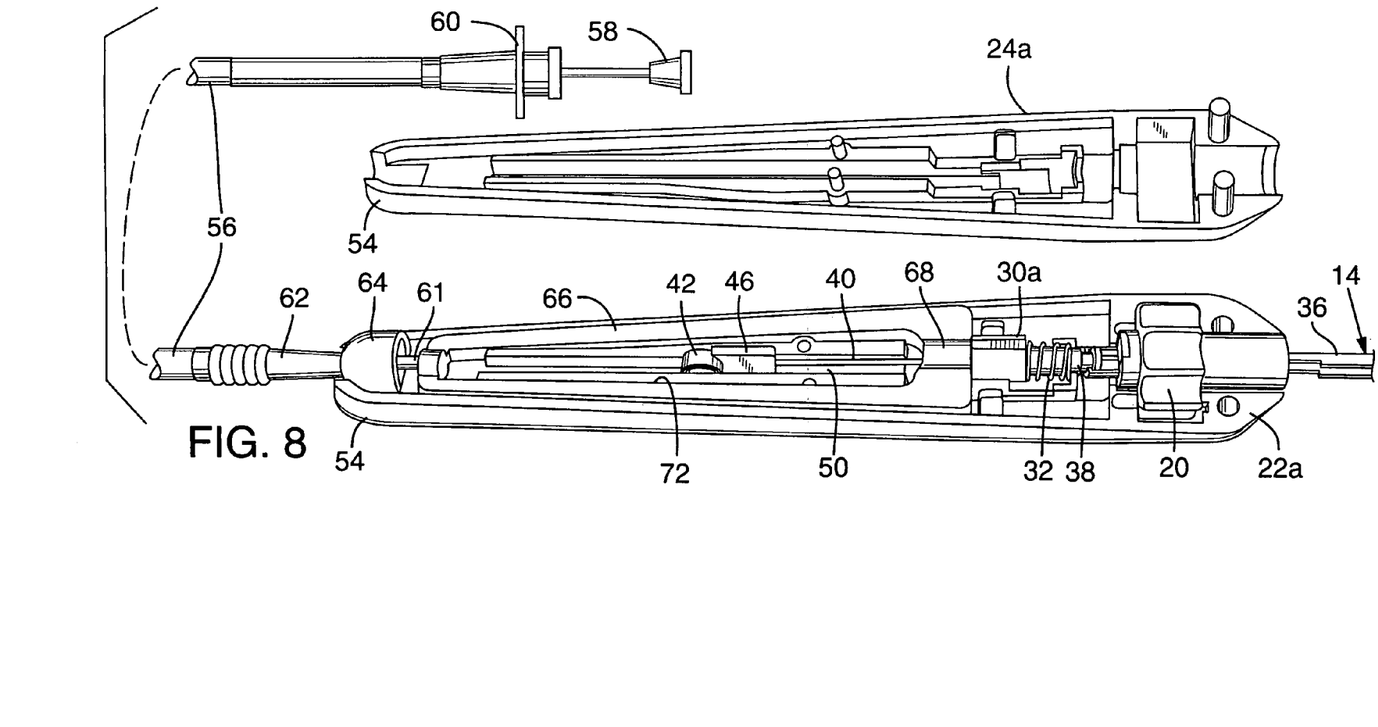
FIG. 8 is an exploded view with part of the shell of the modified clip applier removed, revealing the modified assembly.

Although several different arrangements are possible for transferring the motion and force of the cable release's tail piece 61 into motion of the clip-applying component 36, FIGS. 6 through 8 show one preferred structural arrangement, particularly for use with the VCS clip applier as that instrument is constituted. The internal mechanical aspects of the clip applier handle could be modified or manufactured more efficiently to reflect the omission of the thumb/finger force wings 18, and if so the internal components added pursuant to the invention could be different and simpler.

The tail end 54 of the clip applier's handle 16a is fitted with a female thread in a bell-shaped fitting 64, since the cable release device 52 typically has a male thread on the end of the metal tail or proximal end 62. Thus, the cable release is screwed into the back end of the clip applier, although the two could be manufactured as one single, non-separable unit if desired. The prior art clip applier mentioned above has been sold as a disposable instrument, and this can be a consideration in including a screw fitting. FIG. 8 shows the fitting 64 seated in the tail end of the handle for the purpose of screw assembly with the cable release.

FIG. 6 shows the handle disassembled with the two halves 22a and 24a lying beside the clip advancing and applying assembly which comprises the position adjustment wheel 20 (optional), the stem 14, the clip-applying component 36, the compression spring 32, and a revised movable member 30a (ramps not needed), connected tubular stem extension 38, and the clip magazine rod 40 with its tail part 46. Surrounding the rod 40 is an advancer frame 66 which acts as a linkage member or linkage means within the handle to receive force from the cable release and transfer it ultimately to the clip-applying component 36 to crimp and dispense a clip. In FIG. 6, the rod has been assembled through a hole provided in an upper end 68 of the advancer frame, and the roll-up spring 42 of the clip mechanism is shown held back using a temporary pin 70 that does not form a part of the assembly. The spring 42 is held back for the purpose of assembling the advancer frame and attached components into the handle, then the pin 70 is removed.

FIG. 7 is an enlarged view showing a portion of the device, with the advancer frame 66 assembled into the handle half 22a, and with the roll-up spring 40 returned to its position of bearing against the rod tail part 46. These components 40 and 46 lie within a central elongated opening 72 of the advancer frame, allowing a range of travel for the roll-up spring. As shown, the upper end or forward end 68 of the advancer frame bears against the movable member 30a, thus being positioned to push the movable member 30a forward against the bias of the compression spring 32 when a clip is to be dispensed.

FIG. 8 shows the modified, remotely operable clip applier assembled, except that the handle half or shell 24a has not yet been secured to the handle half 22a. On assembly, the two halves can be retained together by adhesive or by fasteners. Again, the positioning wheel 20 can be eliminated, and preferably is eliminated with the handle being made round so that it can comfortably be oriented in any rotational direction.

As noted above, the remote actuation of the clip applier can be by flexible devices other than the particular type of cable release shown in FIGS. 5-8. A cable device with a coarse screw thread could be provided, so that a twisting motion of an extending distal end piece will rotate a component on a screw thread to move it axially so as to apply axial force at the tail end of the handle, as required to move the linkage member and the movable member forward in the clip applier so as to dispense a clip.

Figure 9:
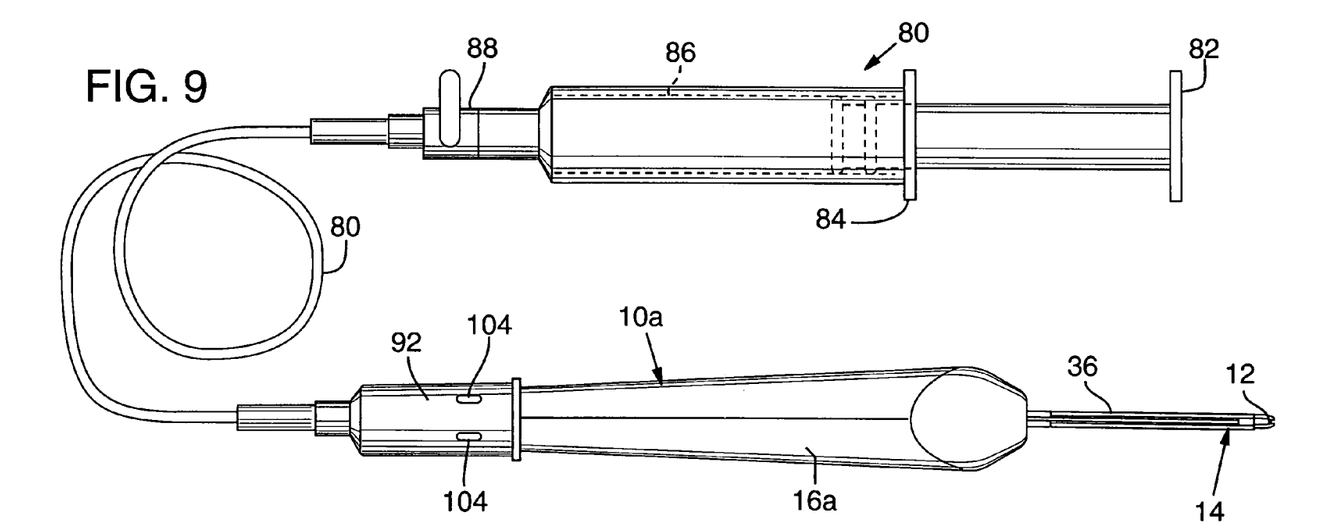
FIG. 9 is a plan view showing an alternate form of the invention.
Figure 10:
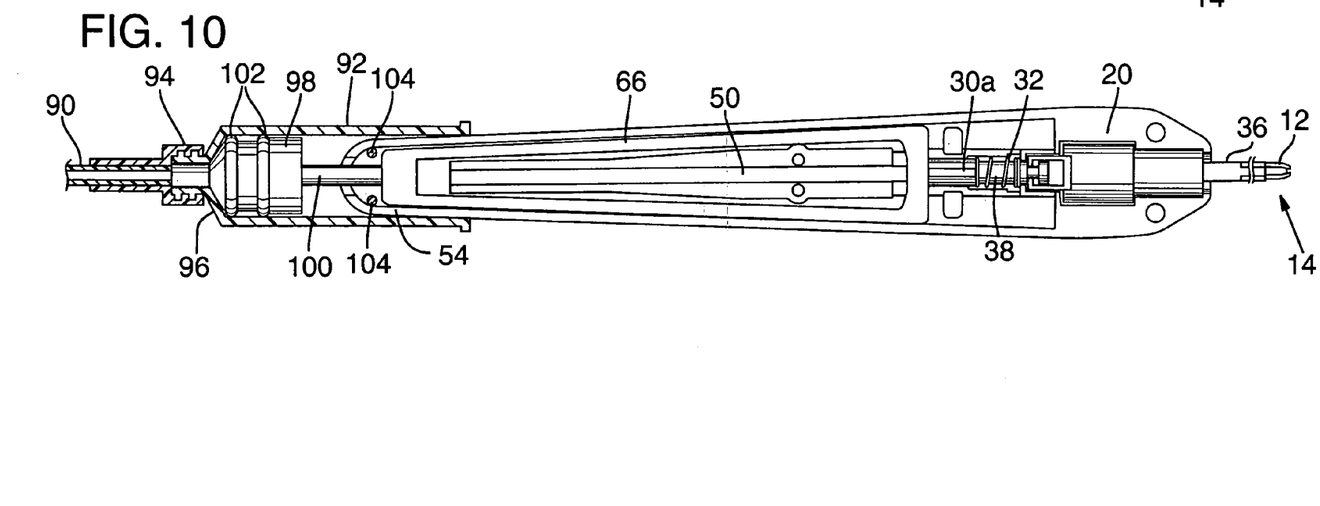
FIG. 10 is a sectional view of the device of FIG. 9.

Another simple alternative is shown in FIGS. 9 and 10, where hydraulic pressure is used to move the linkage means and in turn the movable member, via an alternative form of cable release device. In any of these alternatives the linkage device, i.e. the advancer frame 66, could be integral with the movable member 30a (wings removed) if desired, or differently-designed internal components for applying the requisite axial force to dispense and crimp a clip could be employed, particularly if the clip magazine rod 40 and spring 42 were rearranged in position. What is important is that the flexible actuating device be attached to the tail end of the instrument handle, so as to be capable of delivering a remotely applied force ultimately to dispense and crimp a clip into the desired position without requiring finger/thumb squeezing motion on the handle, particularly near the forward tip of the handle as was required previously.

FIG. 10 is a simplified view, omitting the magazine rod 40 and spring 46, which can be similar to what is shown in the previous drawings. FIG. 9 shows a remote plunger 80, which can be a syringe, e.g. a 10 cc or 20 cc syringe, or an adaptation of a syringe or some other hydraulic piston and cylinder actuator. The plunger 80 has a thumb actuable piston end 82 serving as the plunger, a grip 84 and a cylinder body 86. A valve 88 is shown at the tail end of the cylinder, although this is not needed in normal circumstances. A hydraulic line 90, comprising a tubular sheath which can be intravenous tubing or similar, is filled with hydraulic fluid, as is the cylinder 86, and this line leads to a proximal end cap or fitting 92 that fits onto and is secured to the tail end 54 of the handle 16a of the clip applier 10a. The hydraulic fluid is an internal medium in the sheath effective to transfer motion of the thumb button to motion of the linkage means and movable member, just as the internal cable in the previously described embodiment similarly acted as an internal medium.

As seen in FIG. 10, the hydraulic line 90 is connected via a fitting 94 in this embodiment to a tail end 96 of the distal end fitting 92, which itself comprises another hydraulic cylinder. A piston 98 within the cylinder of the end cap 92 is pushed forward when the thumb button/plunger 82 is pushed down to force hydraulic liquid out of the remote end cylinder 86. This movement of the second piston 98 pushes forward a piston shaft 100, which engages the tail end of a linkage member such as the advancer frame 66 shown. As described previously, this is effective to dispense and crimp a clip from the instrument 10a.

FIG. 10 shows that the second piston 98 has seals 102, which may be annular ridges on a rubber piston. Also, the figure shows fasteners 104 which may be used to secure the proximal end fitting 92 to the tail end of the clip applier handle, and thus the remote actuator can be removable from the clip applier handle, if desired.

Although hydraulic actuation is described above, pneumatic actuation is also possible, with a similar arrangement of piston and cylinder, thumb button, etc., in which case the internal medium of the tubular would be air or other gas.

Actuation of the clip applier can be by foot rather than using a hand operable actuator. The remote actuator can be a foot pedal (not shown), depressed by the person holding the clip applier.

For purposes of understanding the appended claims, it should be clarified that the movable member and the linkage means could comprise a single piece, and in the claims these components are to be construed as either one piece or two. Even though these components are stated as two elements in the claims, the two elements can be connected together or integral and the movable member can be considered as the forward end of that unitary piece, and the linkage member or linkage means can be considered as the rearward portion of the same piece.

The above described preferred embodiments are intended to illustrate the principles of the invention, but not to limit its scope. Other embodiments and variations to this preferred embodiment will be apparent to those skilled in the art and may be made without departing from the spirit and scope of the invention as defined in the following claims.

I claim:

1. A device for applying non-penetrating clips to small blood vessels or other wound sites or tissue separation sites where suturing or other wound closure techniques would be impossible or undesirable, comprising:
   a hand-held clip applier, including:
      a handle suitable for gripping in the hand of a surgeon,
      a clip storing and dispensing stem extending from a forward end of the handle, the stem having a tip at a remote end for dispensing and serially applying metal clips in non-penetrating engaging configuration against sections of tissue on either side of a wound or tissue separation to clamp the two sections of tissue together, upon the receipt of mechanical force to a clip-applying component of the stem,
      a movable member within the handle which, when caused to move by a force applied from outside the handle, is effective to cause movement of the clip-applying component in the stem so as to cause dispensing and application of a clip, and
      linkage means engaged with the movable member within the handle and extending to a position in the handle capable of receiving a pushing force from the exterior of the handle, and
   a flexible cable release device comprising a cable sheath, and an internal cable capable of delivering a compressive pushing force through the sheath, a hand operable actuator at a remote hand-grippable end of the cable release, remote from the clip applier, for applying a pushing force to slide the cable through sheath so as to cause extension of a pusher tailpiece out of a proximal end of the cable sheath when the hand operable actuator is engaged, the sheath at the proximal end having means for connection to the handle of the hand-held clip applier in a position to apply force to the linkage means in the handle by motion of the pusher tailpiece, thus advancing the linkage means and movable member within the handle, and thus advancing the clip-applying component to dispense and apply a clip when the hand operable actuator on the flexible cable release device is pushed, the cable sheath and internal cable being sufficiently flexible as to avoid movement of the tip when the hand operable actuator is moved to apply said pushing force,
   whereby with the cable release device connected to the clip applier the hand-held clip applier can be held very steadily in one hand with its tip under a microscope while the force to apply a clip is supplied at the remote end of the cable release device, avoiding any movement of the tip at the instant of clip application.

2. The device of claim 1, wherein the handle is round so as to be capable of comfortable hand gripping in any rotational orientation.

3. A device for applying non-penetrating clips to blood vessels or other wound sites or tissue separation sites where suturing or other wound closure techniques would be impossible or undesirable, comprising:
   a hand-held clip applier, including:
      a handle suitable for gripping in the hand of a surgeon,
      a clip storing and dispensing stem extending from a forward end of the handle, the stem having a tip at a remote end for dispensing and serially applying metal clips in non-penetrating engaging configuration against sections of tissue on either side of a wound or tissue separation to clamp the two sections of tissue together, upon the receipt of force to a clip-applying component of the stem,
      a movable member within the handle which, when caused to move by a force applied from outside the handle, is effective to cause movement of the clip-applying component in the stem so as to cause dispensing and application of a clip, and
      linkage means adjacent to the movable member within the handle and extending to a position in the handle capable of receiving a force from the exterior of the handle, and
   a flexible remote force-transmitting device comprising a tubular sheath, and an internal movable medium capable of delivering a force through the tubular sheath, a remote actuator at a remote end of the flexible device, remote from the clip applier, for applying a force to slide the movable medium through the sheath so as to cause movement of a tailpiece at a proximal end of the tubular sheath when the remote actuator is engaged, the sheath at the proximal end being connected to the handle of the hand-held clip applier in a position to apply force to the linkage means in the handle by motion of the tailpiece, thus moving the linkage means and movable member within the handle, and thus advancing the clip-applying component to dispense and apply a clip when the remote actuator on the flexible force-transmitting device is engaged, the tubular sheath and medium being sufficiently flexible as to avoid movement of the tip when the remote actuator is engaged and moved to apply said force,
   whereby with the remote flexible force-transmitting device connected to the clip applier the hand-held clip applier can be held very steadily in one hand, and can be gripped at any location desired along the length of the handle, while the force to apply a clip is supplied at the remote end of the flexible device, avoiding any movement of the tip at the instant of clip application.

4. The device of claim 3, wherein the remote flexible force-transmitting device has a threaded fitting at its proximal end, the tail end of the handle of the clip applier having a mating thread so that the flexible device is removable from the clip applier.

5. The device of claim 4, wherein the flexible force-transmitting device comprises a cable release device, said movable medium comprising an internal cable in the tubular sheath and the actuator comprising a thumb button.

6. The device of claim 3, wherein the remote flexible force-transmitting device comprises a hydraulic line containing liquid as said movable medium, and wherein the remote end of the flexible device has a piston and cylinder connected to put pressure on the liquid when the actuator is depressed, to force the liquid through the hydraulic tube, and said proximal end of the flexible device having a second piston and cylinder with the piston connected to said tail piece, so that the linkage means and movable member are moved hydraulically when the actuator is depressed.

7. The device of claim 6, wherein the actuator comprises a thumb button connected to the piston at the remote end of the flexible device.

8. The device of claim 3, wherein the handle is round so as to be capable of comfortable hand gripping in any rotational orientation.

9. A method for applying non-penetrating surgical clips to blood vessels or other wound sites or tissue separation sites where suturing or other wound closure techniques would be difficult, awkward or undesirable, comprising:

provideing a hand-held clip applier which includes:

a handle suitable for gripping in the hand of a surgeon, a clip storing and dispensing stem extending from a forward end of the handle, the stem having tip at a remote end for dispensing and serially applying metal clips in non-penetrating engaging configuration against sections of tissue on either side of a wound or tissue separation to clamp the two sections of tissue together, upon the receipt of force to a clip-applying component of the stem, a movable member within the handle which, when caused to move by a force applied from outside the handle, is effective to cause movement of the clip-applying component in the stem so as to cause dispensing and application of a clip, and linkage means adjacent to the movable member within the handle and extending to a position in the handle capable of receiving a force from the exterior of the handle, and providing a flexible remote force-transmitting device connected to the handle of the clip applier, the force-transmitting device comprising a tubular sheath, and an internal movable medium capable of delivering a force through the tubular sheath, a remote actuator at a remote end of the flexible device, for applying a force to slide the movable medium through the sheath so as to cause movement of a tailpiece at a proximal end of the tubular sheath when the actuator is engaged, the sheath at the proximal end being connected to the handle of the hand-held clip applier in a position to apply force to the linkage means in the handle by motion of the tailpiece, thus moving the linkage means and movable member within the handle, and thus advancing the clip-applying component to dispense and apply a clip when the actuator on the flexible force-transmitting device is engaged, positioning the tip of the clip applier in an appropriate position to connect tissue, and effecting dispensing and application of a clip at the site to be closed by engaging the remote actuator at the remote end of the flexible device, the engaging of the actuator not being performed by the hand holding the handle of the clip applier.

10. The method of claim 9, wherein the actuator is engaged by a person other than the person holding the handle of the clip applier.

11. The method of claim 9, wherein the actuator comprises a foot pedal and is depressed by the person holding the clip applier.

* * * * *